(12) United States Patent
Alander et al.

(10) Patent No.: US 7,422,757 B2
(45) Date of Patent: Sep. 9, 2008

(54) TABLETTING PROCESS

(75) Inventors: Jari Alander, Karlshamn (SE); Staffan Norberg, Karlshamn (SE); Henri Hansson, Helsingborg (SE); Marianne Svärd, Veberöd (SE); Lars Hovgaard, Farum (DK)

(73) Assignee: Galencia AB, Malmo (SE)

( * ) Notice: Subject to any disclaimer, the term of this patent is extended or adjusted under 35 U.S.C. 154(b) by 737 days.

(21) Appl. No.: 10/501,873

(22) PCT Filed: Jan. 21, 2003

(86) PCT No.: PCT/SE03/00093

§ 371 (c)(1),
(2), (4) Date: Sep. 14, 2004

(87) PCT Pub. No.: WO03/061630

PCT Pub. Date: Jul. 31, 2003

(65) Prior Publication Data

US 2006/0182799 A1     Aug. 17, 2006

(30) Foreign Application Priority Data

Jan. 21, 2002   (SE)   .................................... 0200154

(51) Int. Cl.
*B29C 43/02*     (2006.01)
*B29B 9/00*      (2006.01)

(52) U.S. Cl. ..................... 424/464; 264/115; 264/122; 264/123; 424/490

(58) Field of Classification Search ...................... None
See application file for complete search history.

(56) References Cited

U.S. PATENT DOCUMENTS

| 4,568,547 | A  | * | 2/1986 | Herschler ................... 514/772 |
| 4,935,246 | A  |   | 6/1990 | Ahrens |
| 6,248,363 | B1 | * | 6/2001 | Patel et al. .................. 424/497 |
| 6,541,025 | B1 | * | 4/2003 | Kershman et al. ........... 424/439 |
| 2005/0084526 | A1 | * | 4/2005 | Alander et al. .............. 424/464 |
| 2006/0115524 | A1 | * | 6/2006 | Eliasen ....................... 424/451 |
| 2006/0147529 | A1 | * | 7/2006 | Klokkers et al. ............ 424/469 |

FOREIGN PATENT DOCUMENTS

| EP | 0 455 391 A1 | 11/1991 |
| EP | 0 841 062 A1 | 5/1998 |
| EP | 0 911 032 A1 | 4/1999 |

* cited by examiner

*Primary Examiner*—Mary Lynn F Theisen
(74) *Attorney, Agent, or Firm*—Birch, Stewart, Kolasch & Birch, LLP

(57) ABSTRACT

The invention refers to a process for the preparation of a self-dispersing or self-emulsifying tablet, wherein a heated granulation mixture containing an active lipophilic substance and a surfactant is granulated into granules, said granules are cooled to a semi-solid state, said semi-solid granules are mixed with one or more fillers to cover the surface of the granules, distribution, the sieved granules are mixed with tabletting aids, and said mixture is compressed into tablets. The granulation mixture can also contain a lipid and/or filler. The invention also refers to tablets prepared by said processes.

9 Claims, 1 Drawing Sheet

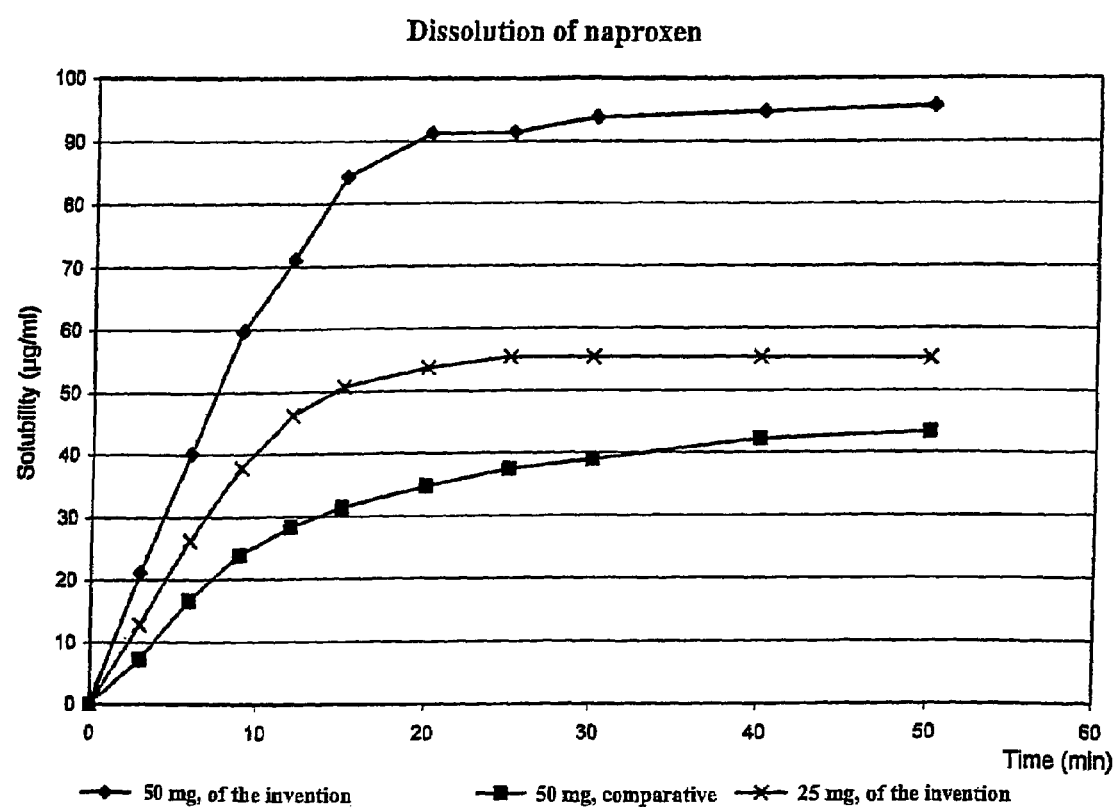
FIGURE

TABLETTING PROCESS

The present invention refers to a process for preparing self-dispersing or self-emulsifying tablets containing a lipophilic substance, as well as to tablets obtained by said process.

BACKGROUND

Poorly soluble active drug substances most often present problems in the manufacture of drug formulations. The water solubility is crucial for absorption and hence bioavailability in the case of the most important route of absorption, passive diffusion. In order to overcome a solubility problem, the formulator is compelled to either increase the solubility on the molecular level by creating a pro-drug or by adding solubility enhancing additives or excipients. The second alternative often includes excipients of lipophilic character like oils. In addition surface-active agents, or detergents, are added in order to create an emulsion. The created emulsion could be thermo-dynamically stable, i.e. a micro emulsion. Said formulations are mostly intended for use as wet systems as mixtures or soft gelatine capsules.

It is well known that lipophilic substances with a very low solubility in water will have a higher bioavailability when administered in a microemulsion, see for instance "Lipid micro emulsions for improving drug dissolution and oral absorption: physical and biopharmaceutical aspects." Constanttinides, P. P. (1995) Pharmaceutical Research, 12, (11) 1561-1572; and "Enhanced intestinal absorption of an RGD peptide from water-in-oil micro emulsions of different composition and particle size", Constantinides, P. P. et al., (1995) Journal of controlled release 34, 109-116; and "Lipid based vehicles for the oral delivery of poorly water soluble drugs", Humberstone, A. J. and Charman, W. N.; (1997) Advanced Drug Delivery Reviews, 25, 103-128.

Tablets are in general the preferred dosage form, being comparatively less expensive to manufacture, easy to store and administer. There is, however, no general way to formulate poorly soluble lipophilic drug substances as tablets wherein the total lipophilic system constitutes a substantial quantity of the tablet weight. This is due to general disturbances and breakage in the interparticulate bonding forces known to be generated by lipophilic substances.

PRIOR ART

A number of references are known referring to inclusion of a microemulsion in a solid dosage form in order to replace costly an inconvenient capsule forms for administration of drugs with improved bioavailability.

Self-emulsifying controlled release tablets for oral delivery of hydrophobic drugs are described by Schwartz, J., et al. in no. 6209 from the 27$^{th}$ Proc Int'l. Symp. Control. Rel. Bioact. Mater. (2000) Controlled Release Society, Inc., and in no. 6107 from the 28$^{th}$ Proc Int'l. Symp. Control. Rel. Bioact. Mater. (2001) Controlled Release Society, Inc. The drug is contained within the oil droplets of the formed emulsion. The self-emulsifying composition is then entrapped into a water swellable gel-forming polymeric matrix and compressed into tablets. The disclosed formulations utilises the formation of a gel-forming matrix for creating diffusion controlled release tablets.

U.S. Pat. No. 4,935,246, Hoechst Aktiengesellschaft, discloses a process for the coating of granules containing wax-like substances in a special equipment similar to a spheroniser. The described process is a melt coating of granules with a wax-like substance that softens during heating. The end product is a granule having a wax-like coating and the process requires heat input in order to produce said coating. The wax-like substance could include an active compound and further a non-wax-like auxiliary. No surfactants are included and no tablet processing has been evaluated.

EP 0 841 062 A1, Daiichi Pharmaceutical CO. LTD., discloses a process for producing a granular preparation, wherein particles are prepared by melt granulation of a powdered low-melting oily substance and a powdered medicine, and the resulting particles are coated with a finely powdered hydrophobic and oil-absorbing high polymeric compound by melt coating. The powdered low-melting oily substance is characterised as a fat or an oil, i.e. glycerol monostearate. The hydrophobic and oil-absorbing high polymeric compound is ethyl cellulose. The purpose of the operation is to avoid caking and reduce bitter taste. Also controlled release is mentioned. No tablet processing has been evaluated.

There is, however, still a need of a process for production of self-dispersing or self-emulsifying tablets, wherein the total lipophilic content constitutes a substantial amount, in order to increase the solubility of a lipophilic active substance.

BRIEF DESCRIPTION OF THE DRAWING

The FIGURE shows a diagram of the dissolution profiles of naproxen tablets, 50 and 25 mg, of the invention, compared to a comparative naproxen tablet, 50 mg, in 500 ml purified water.

DESCRIPTION OF THE INVENTION

It has now been found that a self-dispersing tablet containing a lipophilic active substance with low solubility in water can be prepared from granules by a conventional tabletting method, wherein granules are formed from a lipophilic granulation mixture containing a surfactant and the lipophilic active substance, which granules are allowed to solidify in a size range suitable for tablet production, and just before solidifycation are covered by a fine powdered material, which is adhered to the surface of the granules, in order to improve the tabletting properties. When the tablet is dissolved in water, gastric juice or gastrointestinal fluids a dispersion or emulsion of the lipophilic active substance is spontaneously formed.

Tablets are conventionally prepared by compressing a powder or granules or a mixture thereof. The most important properties of the powder and granules for manufacturing of tablets are flowability, compactability and homogeneity in order to produce tablets having a sufficient hardness, good weight control and good dose homogeneity. Granulation is the process in which powder particles are made to adhere to form larger particles i.e. granules. The granulation of powder can be performed in several ways, such as wet, dry or melting processes. The distinct difference between wet and melt granulation is that wet granulation is followed by a drying step where the liquid part of the granulation medium is dried off. Melt granulation on the other hand includes a cooling step during which the melted material solidifies.

The invention refers to a process for the preparation of a self-dispersing or self-emulsifying tablet, which is characterised by the following steps, granulation of a heated granulation mixture containing an active lipophilic substance and a surfactant into granules, cooling said granules to a semi-solid state, mixing said semi-solid granules with one or more fillers to cover the surface of the granules, sieving of the covered granules into a size below 1 mm, mixing of the sieved granules with tabletting aids, and compressing said mixture into tablets.

The granulation mixture is cooled under agitation and the filler is added during the solidifying process thereby creating a solid lipophilic core including surfactant and lipophilic active substance covered with the filler material.

According to another aspect the invention refers to a process for the preparation of a self-dispersing or self-emulsifying tablet, which is characterised by the following steps, granulation of a heated granulation mixture containing an active lipophilic substance, a lipid and a surfactant into granules, cooling said granules to a semi-solid state, mixing said semi-solid granules with one or more fillers to cover the surface of the granules, sieving of the covered granules into a size below 1 mm, mixing of the sieved granules with tabletting aids, and compressing said mixture into tablets.

The granulation mixture is cooled under agitation and the filler is added during the solidifying process thereby creating a solid lipophilic core including surfactant, lipid and lipophilic active substance covered with the filler material.

Another aspect of the invention refers to a process that is characterised by the following steps, granulation of a heated granulation mixture containing an active lipophilic substance, a lipid, a surfactant and one or more fillers into granules, cooling said granules to a semi-solid state, mixing said semi-solid granules with one or more fillers to cover the surface of the granules, sieving of the covered granules into a size below 1 mm, mixing of the sieved granules with tabletting aids, and compressing said mixture into tablets.

The granulation mixture is cooled under agitation and the filler is added during the solidifying process thereby creating a solid lipophilic core including lipid, surfactant, filler and lipophilic active substance covered with the filler material.

Still another embodiment of the invention refers to a process that is characterised by the following steps, granulation of a heated granulation mixture containing an active lipophilic substance, a surfactant and one or more fillers into granules, cooling said granules to a semi-solid state, mixing said semi-solid granules with one or more fillers to cover the surface of the granules, sieving of the covered granules into a size below 1 mm, mixing of the sieved granules with tabletting aids, and compressing said mixture into tablets.

The granulation mixture is cooled under agitation and the filler is added during the solidifying process thereby creating a solid lipophilic core including surfactant, filler and lipophilic drug substance covered with the filler.

The composition of the granulation mixture is dependent on the process to be used, which in turn is dependent on the active substance to be dissolved or dispersed. Lipid and surfactant can be mixed in different proportions and in different qualities producing granules with different physical and chemical properties.

The granulation mixture of lipid, surfactant and lipophilic active substance will, in contact with water or gastric fluids, be able to form an emulsion. An emulsion is a dispersion of one phase in another, such as oil in water, and the surfactants act as stabilisers of the emulsion. An emulsion is not thermodynamically stable and the formation thereof requires an energy input, e.g. by the peristalsis. A kinetically stable, finely dispersed emulsion may remain finely dispersed for a relatively long time depending on the composition.

The granulation mixture of lipid, surfactant and lipophilic active substance can, in contact with water or gastric fluids, also be able to form a dispersed liquid crystalline phase.

When lipid, water and surfactant are mixed, e.g. by the peristalsis, liquid crystalline phases can also be obtained, such as lamellar, hexagonal, reversed hexagonal and cubic liquid crystal phases. Just as with emulsions the liquid crystalline phases require an energy input.

Different phases of the three components lipid, surfactant and polar liquids are described in for instance Jönsson et al. "Surfactants and Polymers in Aqueous Solutions" Wiley (1999). Evans and Wennerström "The Colloidal Domain, where physics, chemistry and biology meet", Wiley (1999).

The type of lipid to be used in the process of the invention is determined by the melting point and the solubility properties of the active substance. Lipids to be used in the process of the invention should preferably have a melting point above about 30° C. They can for example be selected from the hard fats; hydrogenated coco-glycerides, having a melting point around 34° C., and hydrogenated palmkernel oil, melting point around 35° C. Also hydrogenated special oils can be used, such as hydrogenated arachis oil, melting point around 35° C., and powdered fats, such as hydrogenated rapeseed oil, melting point around 60° C., and hydrogenated soybean oil, melting point around 66° C.

The use of lipids in tablet compositions imposes a binding reducing property that is dependent on the melting temperature, concentration of lipid and choice of other excipients. An oily component tends to break the interparticulate bonds and reduce the tablet strength and also to increase the capping and laminating tendencies of the compact. In order to reduce these problems and still allow a high concentration of lipid in the tablet formulation the lipid surface must be minimised and the powder surface maximised. This is achieved by adding a fine powder material to the lipid granules before solidification. The powder material will adhere to the lipid granule surface and thereby improve the bonding properties in the tabletting process. Also the flowability is markedly enhanced. The choices of additional tabletting aids are also of importance.

The produced lipophilic granules are by this way very suitable for producing tablets with high contents of oils/fats and thereby ensuring a possibility of a high lipid load in the tablet formulation due to improved flow characteristics and compression properties.

The surfactant is preferably selected from the group consisting of fatty acid esters of glycerol and fatty acid esters of polyethylene glycol.

The granulation can be performed in different ways using mixing or agitation equipment such as a planetary mixer or a high shear mixer. The techniques normally require a discharging step between the granulation and solidifying if not a single processing equipment is used, such as a vacuum/microwave high shear mixer. In order to facilitate the tabletting, the granules should preferably have an average diameter below 1 mm, preferably within the range of 125-710 μm.

The choice of granulation mixture and granulation process depends on the material to be granulated as well as the properties wanted for the granules. In some cases, specific properties of the active substance have to be considered when choosing granulation medium, method of granulation and tablet processing. The compression of the granules is typically performed with low to medium compressive force.

Examples of fillers are the water-insoluble fillers microcrystalline cellulose, talc and dicalcium phosphate, and the water-soluble fillers lactose and isomalt. It should be noticed that the filler to be added to the granulation mixture must not be the same as the filler added to coat or cover the semi-solid granules. The particles of the filler used for covering the granules must, however, be of a specific size. The powder must also be insoluble in the lipophilic granules. According to a preferred aspect the semi-solid granules are covered by a powdered filler having a particle size of 1-250 μm, preferably 5-150 μm, and especially 10-100 μm.

To achieve acceptable tabletting properties when a high ratio of lipid is used in the tablet formulation a binder is typically used. Binders like PVP, cellulose derivatives, pregelatinised starch etc. can be used dissolved in the granulation medium or as dry powders in the final mix. The invention also refers to a process wherein a binder is added to the granules.

Tabletting aids are for example lubricants, such as magnesium stearate, and disintegrants, such as croscarmellose sodium and sodium starch glycolate, and glidants, such as colloidal silicon dioxide. In addition flavourings, colourings and coating agents can be added.

An active substance, preferably a pharmaceutically active substance, which can be administered in a tablet according to the invention in order to improve the bioavailability, is for instance a hydrophobic or lipophilic substance with a low solubility in water. Substances having a log P value (octanol/water) of about >2 are candidates for the process of the invention.

The invention also refers to tablets prepared by the process. Tablets can be manufactured as immediate release tablets but also as controlled release tablets, either with respect to time or place of release. An enteric coating can be added if the active substance is to be released in the intestines. Coatings can also be applied for taste masking or to provide a special colour. The tablets of the invention have a good weight homogeneity and a friability below 1%.

If large amounts of an active substance are to be administered it might be preferred to use another type of tablet, such as a lozenge or a chewable tablet.

When the tablet is brought into contact with water or gastric juice the active substance is spontaneously dispersed and a microemulsion, colloidal emulsion or drops of an emulsion are obtained, which will improve the distribution of the active substance. Disintegration of a lipid/surfactant containing tablet can result in for instance a microemulsion, an emulsion or fine colloidal emulsions, which all improve or facilitate the distribution of a lipophilic drug in the gastrointestinal tract.

EXAMPLES

In Example 1 the model substance curcumine was used. The granulation medium contained active lipophilic substance, lipid and surfactant. Fine powdered filler material was used to cover the lipid granule surface. The used tabletting aids were Isomalt DC-100 and Mg stearate.

In Example 2 the model substance β-carotene was used. The granulation medium contained active lipophilic substance, filler and surfactant. Fine powdered filler material was used to cover the lipid granule surface. The used tabletting aids were microcrystalline cellulose, Povidone and Mg stearate.

In Example 3 the active substance Naproxen was used. The granulation medium contained active lipophilic substance, filler, fat and surfactant. Fine powdered filler material was used to cover the lipid granule surface. The used tabletting aids were Povidone, Isomalt DC-100 and Mg stearate.

In the examples below the following substances are used as surfactants:

Akolip L M, Karlshamns A B, Sweden, a mixture of glycerol esters of C8-C18 fatty acids and macrogolesters of C8-C18 fatty acids (melting point 44° C., HLB-value 14);

Akoline M C M, Karlshamns A B, caprylic/caprylic glycerides (melting point 25° C., HLB-value 5-6);

Tween 80, Sigma-Aldrich Sweden AB, polyoxyethylenesorbitan monooleate (HLB-value 15).

As examples of oil/fat have been used:

Dynasan P 60, Vendico chemical AB, glycerides of saturated fatty acids (melting point approx. 60° C.);

WITEPSOL E 76, Vendico chemical AB, mixture of hard fats (ascending melting point 37.0-39.0° C., solidification point 34-36.5° C.)

As fillers have been used:

PEG 6000, Fluka, Sigma-Aldrich Sweden AB polyethylene glycol (melting point 55-63° C.);

Isomalt P F, Palitinit GmbH, Mannheim, Germany, a mixture of D-glucopyranosido-D-sorbitol and D-glucopyranosido-D-mannitol-dihydrate (particle size 90%<100 μm);

Lactose powder G200, Meggle GmbH, lactose monohydrate (particle size 99%<63 μm);

Talcum, Talc, Apoteket AB produktion & laboratorier, (particle size 99%<63 μm).

As an example of tabletting aids has been used:

Povidone K25, ISP, USA, 1-ethenyl-2-pyrrolidinone homopolymer (particle size 90%>50 μm and 50%>100 μm);

Avicel PH-102, cellulose, microcrystalline, FMC International, Ireland (nominal mean particle size 100 μm)

Isomalt DC-100, Palitinit GmbH, Mannheim, Germany, a mixture of D-glucopyranosido-D-sorbitol and D-glucopyranosido-D-mannitol-dihydrate in granulated form (particle size 50%>250 μm);

Mg-stearate, Peter Greven, The Netherlands,

Example 1

Self Dispersing/Emulsifying Tablets With Model Substance Curcumine

| Granules: | | (w/w) |
| --- | --- | --- |
| Surfactant | Akolip LM | 40% |
| Fat | Dynasan P 60 | 35% |
| Model substance | Curcumine | 15% |
| Surfactant | Akoline MCM | 5% |
| Surface powder Isomalt PF | | 5% |

Half the amount of the fat, Dynasan P 60, was mixed with curcumine and the surfactants Akolip LM and Akoline MCM and heated to 60° C. The oily liquid was slowly added to the rest of the powdered Dynasan P 60 in a high shear mixer forming a granulate mixture. After partial solidification the Isomalt powder was distributed on the formed granules. The granules were passed through a 1.0 mm sieve and allowed rest in room temperature (RT) on trays over night.

| Tabletting: | (w/w) |
| --- | --- |
| Granules | 74.5% |
| Isomalt DC 100 | 25% |
| Mg-stearate | 0.5% |

The produced granules were mixed with Isomalt DC 100 in a Turbula mixer and a second mixing step was performed with Mg-stearate. The tablet mix was passed through a 1.0 mm sieve and transferred to a Diaf TM-20 single stroke tablet press equipped with round, diameter 12 mm punches. Tablets with a total weight of 500 mg and good weight homogeneity and a friability <0.5% were produced.

Example 2

Self Dispersing/Emulsifying Tablets With Model Drug Compound, β-carotene

| Granules: |  | (w/w) |
|---|---|---|
| Surfactant | Akolip LM | 56% |
| Filler | PEG 6000 | 30% |
| Active | β-carotene | 5% |
| Surfactant | Akoline MCM | 2% |
| Surface powder Lactose powder |  | 7% |

The surfactants, Akolip LM and Akoline MCM, are melted and mixed at 70° C. After cooling to about 55° C., β-carotene is added and the mixture is gently stirred until it is dissolved. A granulation mixture is obtained by adding the resulting oily liquid, as granulation medium, on powdered PEG 6000 in a high shear mixer. After partial solidification the lactose powder was distributed on the formed granules. The granules were passed through a 1.0 mm sieve and allowed rest in RT on trays over night.

| Tabletting: | (w/w) |
|---|---|
| Granules | 60.0% |
| Avicel PH-102 | 24.7% |
| Povidone K-25 | 15% |
| Mg-stearate | 0.3% |

The produced granules were mixed with Avicel PH-102 and Povidone K-25 in a Turbula mixer and a second mixing step was performed with Mg-stearate. The tablet mix was passed through a 1.0 mm sieve and transferred to a Diaf TM-20 single stroke tablet press equipped with round, diameter 12 mm punches. Tablets with a total weight of 500 mg and a good weight homogeneity and a friability <0.5% were produced.

Example 3

Self Dispersing/Emulsifying Tablets With Drug Compound, Naproxen

| Granules: |  | (w/w) |
|---|---|---|
| Surfactant | Akolip LM | 25% |
| Fat | Dynasan P 60 | 25% |
| Active | Naproxen | 16% |
| Fat | Witepsol E 76 | 15% |
| Filler | Isomalt PF | 10% |
| Surfactant | Tween 80 | 2% |
| Surface powder Talcum |  | 7% |

The surfactants, Akolip LM and Tween 80 was melted and mixed together with half the amount of the fats, Dynasan P 60 and Witepsol E 76 at 70° C. Naproxen was added and the mixture was gently stirred until dissolved. A granulation mixture was obtained by adding the resulting oily liquid, as granulation medium, on the remaining amount of powdered fat and Isomalt PF in a high shear mixer. After partial solidification the Talcum was distributed on the formed granules. The granules were passed through a 1.0 mm sieve and allowed rest in RT on trays over night.

| Tabletting: | (w/w) |
|---|---|
| Granules | 72.0% |
| Povidone K-25 | 18.0% |
| Isomalt DC-100 | 9.4% |
| Mg-stearate | 0.6% |

The produced granules were mixed with Povidone K-25 and Isomalt DC-100 in a Turbula mixer and a second mixing step was performed with Mg-stearate. The tablet mix was passed through a 1.0 mm sieve and transferred to a Diaf TM-20 single stroke tablet press equipped with round, diameter 10 mm punches. Tablets with a total weight of 440 mg and a good weight homogeneity and a friability <0.5% were produced. The dissolution of tablets containing 50 and 25 mg naproxen, respectively, and prepared according to the invention was investigated in comparison to a comparative tablet containing 50 mg naproxen, prepared as above, but without the surfactant and lipids. The results are presented in the FIGURE.

The invention claimed is:

1. A process for the preparation of a self-dispersing or self-emulsifying tablet, which is characterized in the following steps,
   granulation of a heated granulation mixture containing an active lipophilic substance and a surfactant into granules,
   cooling said granules to a semi-solid state,
   mixing said semi-solid granules with one or more fillers to cover the surface of the granules,
   sieving of the covered granules into a size below 1 mm,
   mixing of the sieved granules with tabletting aids, and compressing said mixture into tablets.

2. A process according to claim 1, which is characterized in the following steps,
   granulation of a heated granulation mixture containing an active lipophilic substance, a lipid and a surfactant into granules,
   cooling said granules to a semi-solid state,
   mixing said semi-solid granules with one or more fillers to cover the surface of the granules,
   sieving of the covered granules into a size below 1 mm,
   mixing of the sieved granules with tabletting aids, and compressing said mixture into tablets.

3. A process according to claim 1 or 2, characterized in that the granulation mixture in addition contains one or more fillers.

4. A process according to claim 1, characterized in that the semi-solid granules are covered by a powdered filler having a particle size of 1-250 μm.

5. A process according to claim 1, characterized in that the surfactant is selected from the group consisting of fatty acid esters of glycerol, and fatty acid esters of polyethylene glycol.

6. A process according to claim 1, characterized in that a binder is added to the semi-solid granules.

7. A process according to claim 6, characterized in that the binder is added to the granulation mixture.

8. A process according to claim 6, characterized in that the binder is added as a dry powder together with the tabletting aids.

9. A tablet, characterized in being prepared by a process according to claim 1.

* * * * *